(12) United States Patent
Inman, Jr.

(10) Patent No.: US 6,580,506 B2
(45) Date of Patent: Jun. 17, 2003

(54) FIBER OPTIC PROBES APPARATUS FOR SPECTROPHOTOMETRY

(75) Inventor: Guy W. Inman, Jr., Hillsborough, NC (US)

(73) Assignee: Leap Technologies, Inc., Carrboro, NC (US)

( * ) Notice: Subject to any disclaimer, the term of this patent is extended or adjusted under 35 U.S.C. 154(b) by 154 days.

(21) Appl. No.: 09/781,138

(22) Filed: Feb. 10, 2001

(65) Prior Publication Data

US 2002/0109845 A1 Aug. 15, 2002

(51) Int. Cl.$^7$ .............................................. G01N 21/59
(52) U.S. Cl. ........................................ 356/436; 385/12
(58) Field of Search ........................... 356/436; 385/12, 385/13

(56) References Cited

U.S. PATENT DOCUMENTS

| | | |
|---|---|---|
| 5,084,614 A | 1/1992 | Berkner |
| 5,381,237 A * | 1/1995 | Sela ............................ 356/436 |
| 5,530,553 A * | 6/1996 | Hsia et al. ................... 356/436 |
| 5,647,838 A * | 7/1997 | Bloomer ...................... 600/111 |
| 5,754,722 A * | 5/1998 | Melling ....................... 385/115 |
| 5,953,477 A | 9/1999 | Wach et al. |
| 6,118,520 A | 9/2000 | Harner |
| 6,169,829 B1 * | 1/2001 | Laming et al. ............... 385/37 |

* cited by examiner

Primary Examiner—Daniel St. Cyr
(74) Attorney, Agent, or Firm—Kenneth S. Watkins, Jr.

(57) ABSTRACT

A fiber optic probe (100) provides in-vitro measurement for measuring fluid media containing bubbles and particulate matter where disturbances to fluid dynamics must be kept to a minimum. The probe transmits light to, and receives light from, the measured fluid media across a light-path gap (119) using two, separate fiber support tubes (107A, 107B) to protect the transmitting and receiving fibers and provide a rigid and resilient structure. Each support tube, containing one or more fibers, is bent ninety degrees in a smooth quarter circle to produce a light path gap that is perpendicular to the longitudinal axis (113) of the probe. A cross-member (125) provides precise alignment of the optical axes or the transmitting and receiving fibers. The small-diameter support tubes reduce hydraulic flow disturbances and debris buildup which would occur with conventional probes during tablet dissolution. The transverse light path gap reduces opportunities for debris buildup and bubble entrapment between transmitting and receiving optical surfaces.

30 Claims, 6 Drawing Sheets

FIBER OPTIC PROBES APPARATUS FOR SPECTROPHOTOMETRY

FIELD OF THE INVENTION

The present invention relates to fiber optic probes for spectrophotometry. In particular, the present invention relates to a fiber optic probe optimized for absorbance measurement applications in fluid media where bubbles, particulate matter, measurement sensitivity, stray light rejection, and flow dynamics are a concern. The present invention further relates to automated, multi-channel spectrophotometric measurements that employ multiple fiber optic probes coupled to either multiple single-channel spectrometers, multiplexed single-channel spectrometers, or single multi-dimensional "imaging" spectrographs that employ a two-dimensional CCD (charge-coupled-device) array as the detection and measurement element.

BACKGROUND OF THE INVENTION

Spectrophotometric absorbance measurements are typically performed by measuring the amount of light ($I_0$) that passes through subject media which contains no sample components of interest and then measuring the amount of light (I) that passes through the subject media that does contain the sample component to be measured. The quantity $I_0$ is referred to as the reference or blank light intensity and the quantity I is referred to as the sample intensity. The concentration of the sample component of interest is proportional to the Absorbance (A), where $A=-\text{Log}_{10}(I/I_0)$.

The terms "spectrograph" and "spectrometer" are often used in reference to the same instrument type. However, a spectrograph is a special case of a spectrometer that uses a stationary grating and has no parts (other than a shutter in some cases) that move during the measurement cycle. Light is instantaneously diffracted horizontally across the surface of a multi-element array detector (CCD or photodiode). Some spectrometers use a motorized grating to scan across the spectrum and direct light through an exit slit onto a single-element detector.

When fiber optic technology is used, light from a source may be transmitted across a light path gap in the subject media by one or more transmitting fibers, and received by one or more receiving fibers which direct the transmitted light to the detection and measurement device. Probes using this approach are referred to as transmittance probes. In a variation of this basic technique, the transmitting and receiving fibers are side by side and a mirror is used to reflect light back through the subject media onto a receiving fibers. This, in effect, doubles the light path gap.

The applications of in situ or remote measurements using fiber optic spectrophotometric probes has increased significantly in step with advances in fiber optic technology, spectrometry and computing hardware, and data collection and processing software. Many commercial systems now support a wide range of in situ spectrophotometric applications which monitor multiple signals from either multiplexed individual spectrometers or single spectrographs employing two-dimensional CCD detector arrays. Only within the last five years have these advances been applied to commercial in situ spectrophotometric monitoring systems targeted to pharmaceutical in vitro dissolution testing.

There have been minimal advances in fiber optic probe design that target the specific needs of pharmaceutical dissolution testing where flow dynamics and particulate interference are primary concerns. The maintenance of constant flow dynamics throughout an in vitro dissolution test is a major concern of pharmaceutical laboratories that are required by law to perform dissolution testing before allowing product dosage forms to be sold. The in vitro dissolution testing must be done in accord with standards and procedures defined by the U.S. Food and Drug Administration and the United States Pharmacopoeia. Published studies have shown that large diameter probes alter flow dynamics and cause observed tablet dissolution rates to be abnormally high.

Fiber optic probes used in all current commercial in situ dissolution testing systems are based on insertion probe designs commonly employed in industrial environments where the probe must be highly rugged and cylindrical. Typically, the transmitting and receiving fibers are side-by-side (parallel) and in the same enclosure which has a uniform diameter over the submerged portion of the probe. The uniform diameter allows the probe to be readily inserted into a reactor, flowing stream, or other vessel where a seal between the probe and vessel walls is required. Dissolution testing and other forms of laboratory-based testing, where fluid media in a wide-mouthed, unsealed vessel is monitored, have no such requirements for extreme ruggedness or cylindrical configuration.

OBJECTS AND SUMMARY OF THE INVENTION

Therefore, an object of the present invention is to fully meet the needs of laboratory-based, in vitro pharmaceutical dissolution testing and other types of laboratory testing with similar requirements.

Another object of the present invention is to provide a probe for sampling fluids which provides a direct light path between a transmitting optic fiber and a receiving optic fiber without the requirement for additional path-altering optic elements such as mirrors or prisms.

Another object of the present invention is to provide a probe for sampling fluids which improves the optic efficiency over earlier designs, allows small-diameter optic fibers and support tubes to be used to reduce flow disturbances in the sample gap area.

Yet another object of the present invention is to provide a probe for sampling fluids which reduces or eliminates probe surfaces that can trap air bubbles or accumulate debris in the sample gap.

The present invention is a fiber optic probe that includes an open, fine-bodied probe structure and an efficient means of transmitting source light through fluid media to one or more receiving fibers. The probe structure offers minimal resistance or disturbance to fluid flow in the sample area and thus minimizes any affect on solution hydrodynamics or turbulence. The features of one embodiment of the invention are an open structure, very low probe displacement volume and surface area, a light path gap that is perpendicular to the longitudinal axis of the probe in the preferred embodiments, and an efficient means of coupling transmitted light to the receiving fiber that employs no internal optic elements or fiber end modifications. The latter feature also ensures that the invention has excellent stray-light rejection characteristics. Because of its simplicity the probe is economical to manufacture.

Elimination of a discrete light reflecting or refracting element such as a mirror or prism increases the efficiency of light throughput for a given fiber size. Thus it becomes possible to employ smaller diameter fibers than would be required when a discrete light reflecting or refracting element is present. This translates to a significant advantage over conventional designs when the present invention is coupled with a multi-channel "imaging" spectrograph based on a two-dimensional CCD array detector.

Coupling to the spectrograph is achieved by bringing the distal ends of receiving fibers together into a vertical array bundle that is mounted to the input of a commercially available spectrograph. The spectrograph employs a fixed grating to diffract the light across the wavelength range of interest and additional optic elements to image the multiple light beams onto the surface of a two-dimensional CCD array. Example arrays are composed of 256×256, 512×512, 1024×1024, and other variations on detecting pixel configurations. A CCD spectrometer that could formerly support a maximum of six to eight probes using prisms and 600 µm fibers would now be able to support 12 or 18 "transverse light path" probes of the present invention design using 300 or 200 µm fibers. This translates to a significant advantage in the application of dissolution testing which is done in groups of six to eight vessels. The CCD spectrometer in the previous example would now be able to support up to three dissolution baths or experiments at the same time.

The probe of the present invention significantly reduces the cost of equipment required to automatically monitor multiple dissolution tests by elimination of expensive optic elements in the optic probe and increasing the number of channels which one spectrograph can monitor. Multi-channel instruments can monitor more probes of the current design as compared to conventional probes.

In use, one or more probes are inserted into the reference fluid media and the reference intensities are measured and recorded. If the concentrations of chemical species are to be measured, then the probes will be inserted into solutions containing a known concentration of reference standard chemical. The reference standard absorbance values will be measured and response factors calculated for each probe. These factors will be used to convert sample absorbance values into concentration values. The probes are then rinsed and inserted into the sample fluid media and monitoring of the sample intensities is performed according to the requirements of the particular application.

In the example application of pharmaceutical dissolution testing, the probes are placed into standard, wide-mouthed dissolution vessels from above the fluid media surface. Typically they are held in place by a suitable clamp or holder for the duration of the test, or they may be periodically raised above the sampling point by an automated mechanism for periods of time when measurements are not being made. The latter action may be needed to reduce effects on solution hydrodynamics produced by conventional insertion probes. The clamp that holds the probe structure must be adjustable to allow for different sampling heights that correspond to different solution volumes that may be employed during the dissolution test. The USP standard sampling point is half way between the top of the stirring element (paddle or basket) and the top of the test solution. Thus the distance from the light path gap to the vessel cover will vary depending on the solution volume. The clamp must allow the operator to properly configure the probe "sampling height" prior to starting the test.

During the course of sample measurements, bubbles may be produced as a result of liquid media de-aeration. In some applications, as in pharmaceutical dissolution testing of dissolving tablets, particulate matter will also be present during the entire measurement period. The open structure and transverse light path of the present invention helps ensure that particulate matter and bubbles will not be trapped in the light path gap and produce erroneous absorbance measurements. The low displacement volume and surface area of the present design allows the probes to remain in the vessels for the duration of the test and obviates the need for an additional automated mechanism to raise the probes above the sampling point.

Together the different embodiments of the present invention form a family of fiber optic probe designs that can accommodate a wide range of sensitivity or light path length requirements for monitoring a variety of pharmaceutical dosage forms during dissolution tests.

BRIEF DESCRIPTION OF THE DRAWINGS

These and other features, aspects and advantages of the present invention will become better understood with regard to the following description, appended claims and accompanying drawings where:

DESCRIPTION OF THE PREFERRED EMBODIMENTS

The following is a description of the preferred embodiments of a fiber optic probe for measuring fluid media and a method for automated, multi-channel spectrophotometric measurements utilizing the probe.

Figure 1:
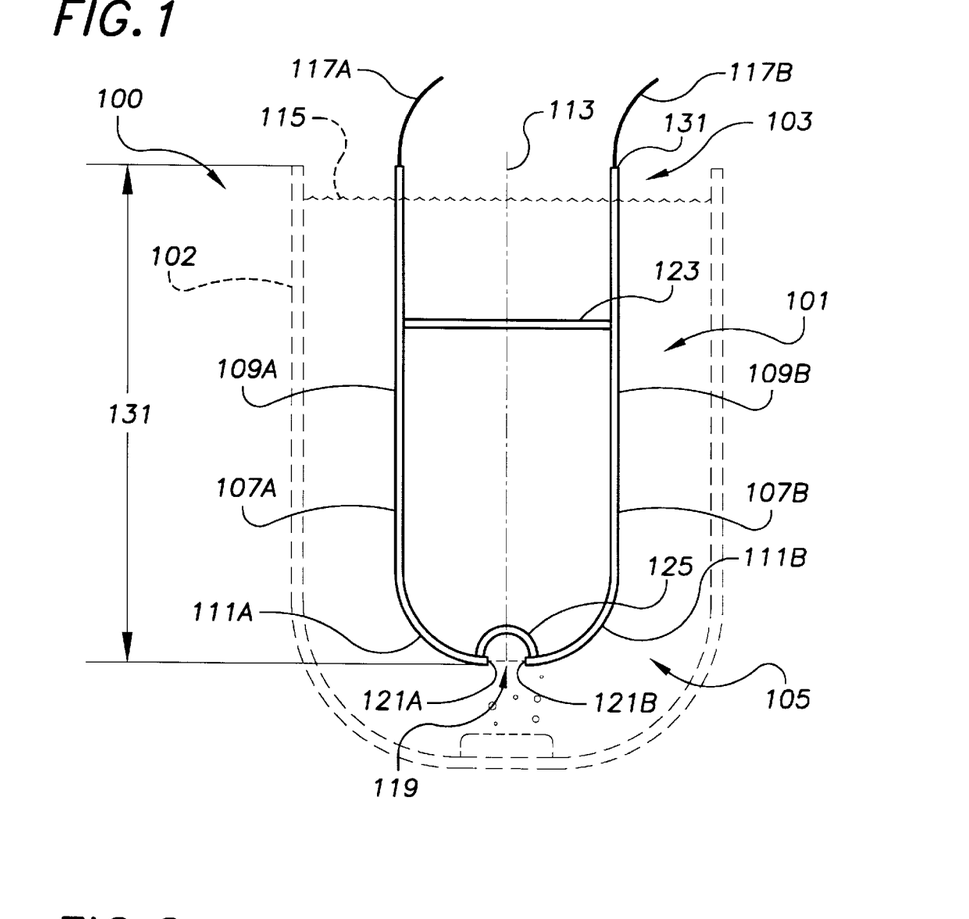
FIG. 1 is a front elevation drawing of a preferred embodiment of the present probe design showing the bent tubing structures which contains the transmitting and receiving fibers and the structural members which tie the two bent structures together and maintain fiber alignment.

FIG. 1 shows a optic fiber probe 100 according to a preferred embodiment of the present invention. Probe 100 comprises an elongated body portion 101, proximate end portion 103, and distal end portion 105. In the preferred embodiment, probe 100 comprises two support members or tubes 107A and 107B. Tubes 107A and 107B comprise elongated tube portions 109A and 109B and curved tube portions 111A and 111B.

In the preferred embodiments, elongated tube portions 109A and 109B of elongated body portion 101 define the longitudinal axis 113 of the probe. Elongated body portion 101 allows immersion of distal end portion 105 to the desired depth below surface 115 of a sample vessel 102. Tube 107A serves as a support member for transmitting optic fiber 117A interior to tube 107A. Likewise, tube 107B serves as a support member for receiving optic fiber 117B interior to tube 107B.

In the preferred embodiments, curved tube portion 111A bends approximately 90 degrees toward tube 107B and curved tube portion 111B bends approximately 90 degrees toward tube portion 111A to define a sample gap 119 between respective distal tube ends 121A and 121B.

In the preferred embodiments, tubes 107A and 107B are connected by upper alignment member or cross-member 123 and lower alignment member or cross-member 125. Cross members 123 and 125 provide structural support for tubes 107A and 107B and provide alignment between optic fiber ends as shown in FIG. 2.

Figure 2:
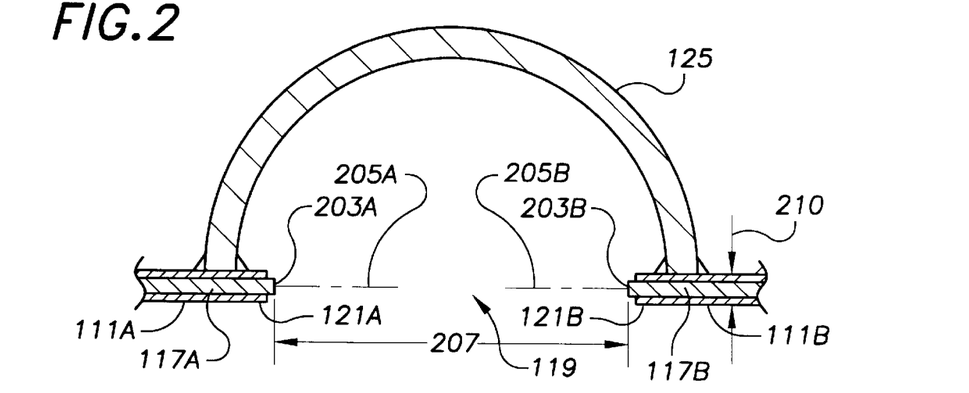
FIG. 2 is a detailed front cross section of the light path gap area of the probe of FIG. 1 showing the transmitting and receiving fiber ends and a structural cross-member used to maintain alignment at the light path gap.

FIG. 2 is a detailed front view cross-section of sample gap 119 area of the optic fiber probe 100 showing optic surface 203A of transmitting optic fiber 117A supported at distal tube end 121A and optic surface 203B of receiving optic fiber 117B supported at distal tube end 121B. Lower cross member 125 supports curved tube portions 111A and 111B so that longitudinal or optic axis 205A of transmitting optic fiber 117A and longitudinal or optic axis 205B of receiving optic fiber 117B are aligned with gap width 207 between optic surface 203A and optic surface 203B. In the preferred embodiments, cross-member 125 supports curved tube end portions 111A and 111B so that longitudinal axes 205A and 205B are parallel. In the most preferred embodiments, longitudinal axes 205A and 205B are coincident.

Sample gap 119 provides a direct path for electromagnetic wave communication between transmitting optic fiber 117A and receiving optic fiber 117B, without path-altering optic elements such as mirrors or prisms. In the preferred embodiments, the electromagnetic communication is light and in the more preferred embodiments, the electromagnetic communication is UV wavelength light. Disposing the optic axis (longitudinal axis of the sample gap 119) perpendicular to longitudinal axis 113 of the probe minimizes entrapment of air bubbles or debris on surfaces of the probe in the gap area which might otherwise interfere with the electromagnetic wave communication between the optic fibers.

In the preferred embodiments, the submerged portions of support tubes 107A and 107B such as curved tube portions 111A and 111B are small diameter tubes having close fit tolerances with interior optic fibers 117A and 117B. Support tubes 107A, 107B, and tube portions 111A and 111B are selected to have a diameter as small as practical to reduce flow dynamic disturbances during tablet dissolution tests.

In the preferred embodiments, optic fibers of diameters of 200–600 micrometers offer a balance of adequate throughput, flexibility, minimum radius of curvature and minimum size for low flow resistance. In the more preferred embodiments, optic fibers 117A and 117B are less than 350 micrometers. A particularly preferred embodiment utilizes 200–300 micrometer fibers such as 300 micrometer optic fibers that efficiently transmit UV light over the wavelength range of 200 to 400 nanometers.

Submerged portions of the tubes must provide adequate strength and support for the fibers with minimum outside diameter for reduced effects on fluid flow in the sample vessel and in the sample area. In the preferred embodiments, support tube members 107A and 107B are 16–24 gauge stainless steel tubing. In the more preferred embodiments, support tubes 107A and 107B are 22 gauge (0.028" OD, 0.016" ID) type 316WSS hypo tubing, standard wall. In the preferred embodiments, the support tube diameter 210 of the submerged tube portions such as elongated body portion 101 and distal end portion 105 is less than 2.0 mm in order to reduce fluid flow effects in the vessel and sample area. In the more preferred embodiments, the support tube diameter of the submerged portions is less than 1.5 mm. In the most preferred embodiments, the support tube diameter at the distal end portion 105 is less than 1.0 mm.

In the preferred embodiments, the support tube diameter at the distal end portion 105 is less than 0.05 of probe length 131 to reduce fluid flow effects in the active sample area. In the more preferred embodiments, the support tube diameter at the distal end portion 105 is less than 0.02 of probe length 131. In the most preferred embodiments, the support tube diameter at the distal end portion 105 is less than 0.01 of probe length 131.

Reduction of the displaced volume of the submerged portions of the probe also reduces flow disturbances resulting from the probe. In the preferred embodiments, the displaced volume of the submerged portion of probe 100 is less than 200 cubic millimeters. In the more preferred embodiments, the displaced volume of probe 100 is less than 100 cubic millimeters. In the most preferred embodiments, the displaced volume of probe 100 is less than 50 cubic millimeters. The displaced volume of the submerged portion of support tubes 107A and 107B is defined as the volume of the portions of probe 100 of FIG. 1 below surface 115 when the probe is positioned in a vessel for dissolution testing purposes.

It is understood that modifications to the embodiments shown, such as non-circular tube cross-sections may be used which are within the scope of the invention. For non-circular cross sections, the effective diameter of the non-circular section is defined as:

$$D(eff)=1.273 \times A$$

Where A is the cross-sectional area of the non-circular cross-section.

In the preferred embodiments, the effective diameter of lower cross-member 125 is dimensioned to the same criteria of support tube diameter 210 at distal end 105 to reduce flow disturbances and to reduce surface area in the sample gap region that would collect residue and bubbles during tablet dissolution events. In the preferred embodiments, no optic elements such as prisms or mirrors are utilized, for example, to produce multiple light path directions in the sample gap area. Such elements increase flow disturbances and increase surface area which might accumulate debris and bubbles during sampling evolutions. A direct light path as shown in FIG. 2 provides a light-efficient gap, allowing small-diameter fibers and support tubes to be used to decrease flow disturbances in the sample gap and surrounding area of the vessel.

Figure 3:
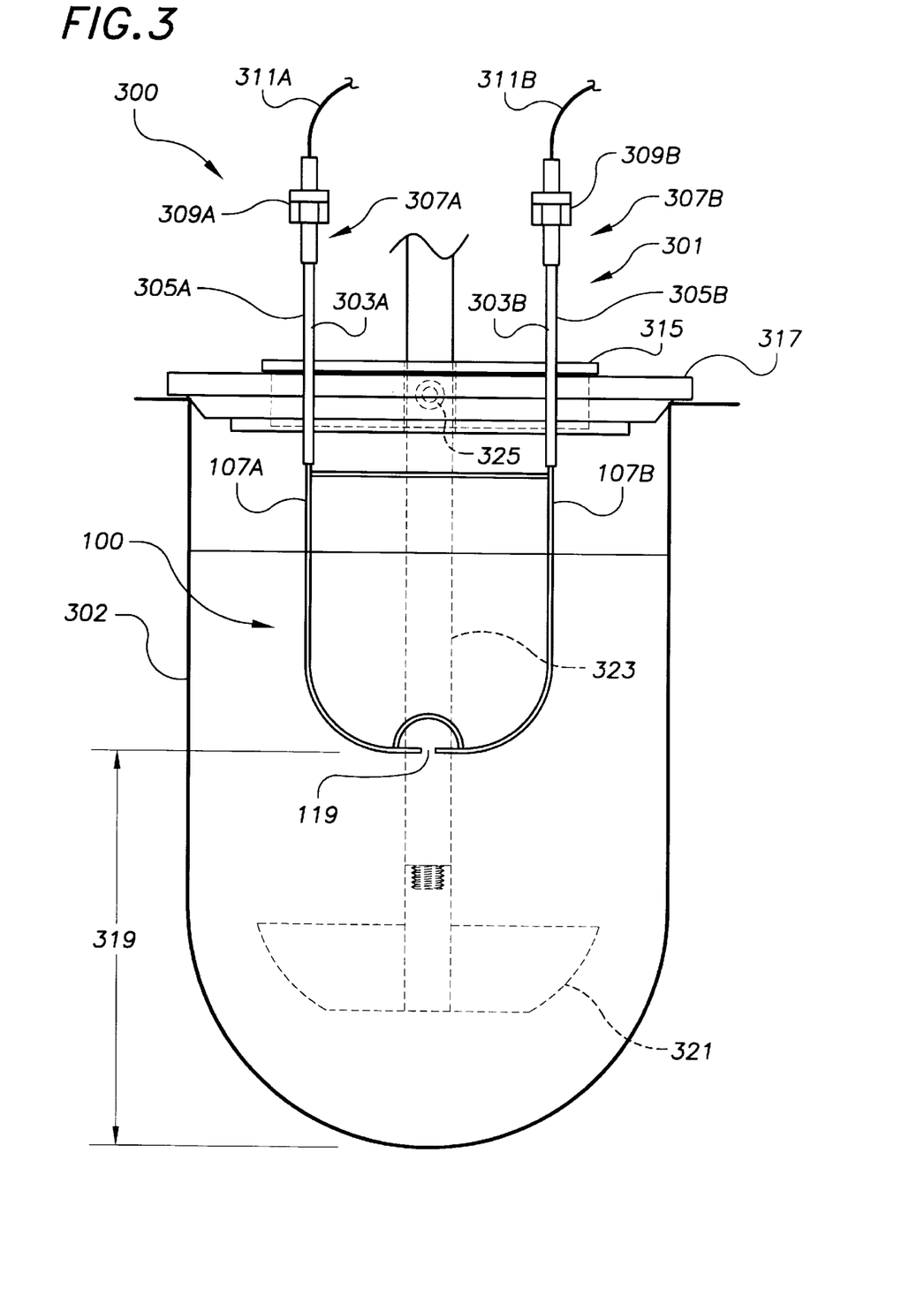
FIG. 3 is a front elevation drawing of an optic probe assembly comprising the optic probe of FIG. 1, and an upper support assembly for supporting the probe in a sample vessel.

FIG. 3 is a front elevation drawing of an optic probe assembly 300 inserted into sample vessel 302. Probe assembly 300 comprises an upper support assembly 301 fixed to an optic probe portion such as optic probe 100 of FIG. 1. Upper support assembly 301 comprises connection tubes 303A and 303B that fit over support tube members 107A and 107B of proximate end portion 103 of FIG. 1.

Connection tubes 303A and 303B comprises bend portions 305A and 305B which provide offset handle portions 307A and 3307B. Handle portions 307A and 307B comprise optic fiber connectors 309A and 309B for connecting optic fibers 311A and 311B from the instrumentation to optic fibers 117A and 117B of optic probe section 100. Probe clamp 315 of vessel cover 317 clamps probe assembly 300 and allows adjustment such as sampling height 319 of sample gap 119. Paddle assembly 321 and shaft 323, shown in phantom lines, provides desired fluid agitation in vessel 302.

Figure 4:
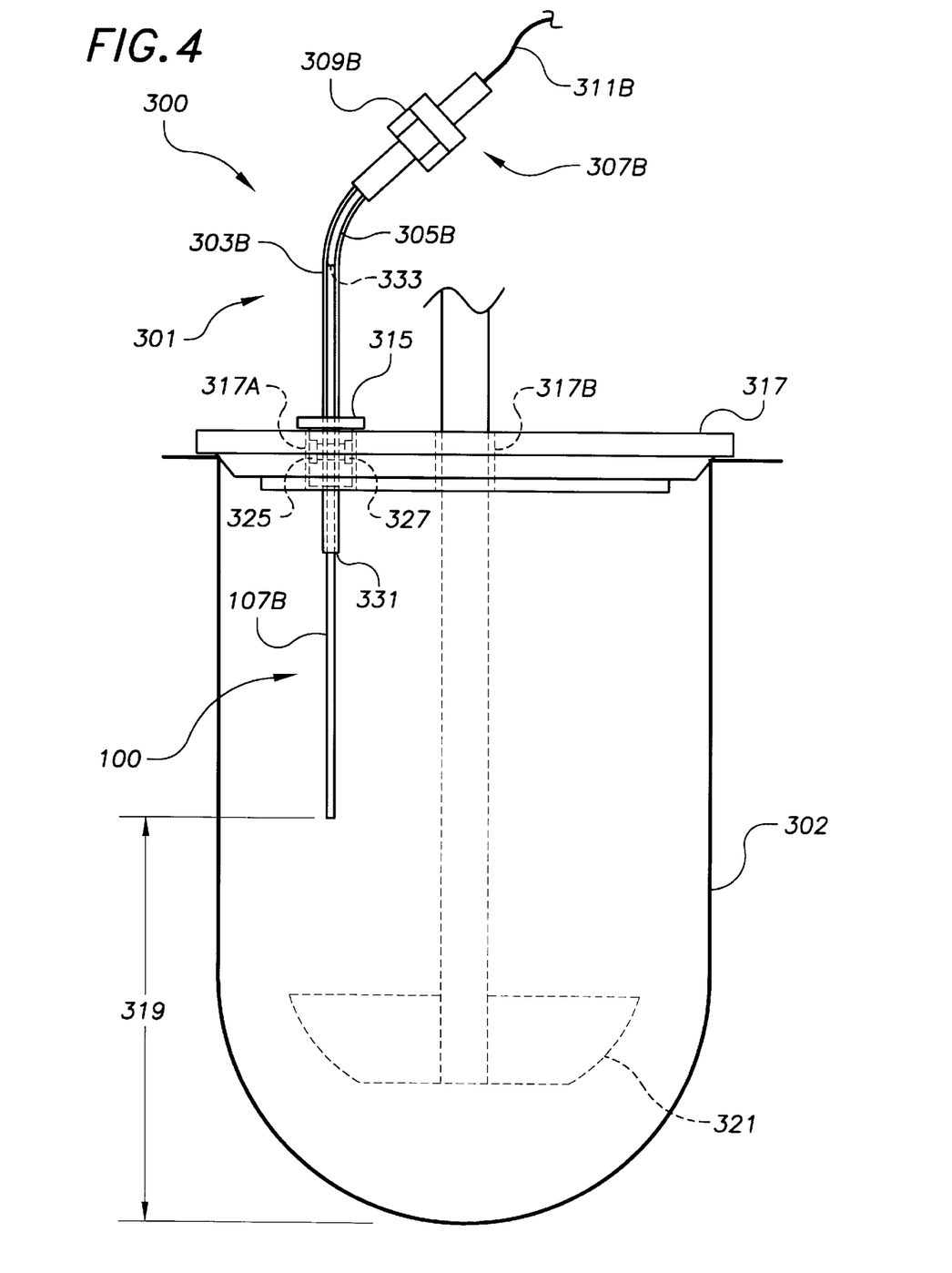
FIG. 4 is a side elevation drawing of the probe assembly of FIG. 3.

FIG. 4 is a side elevation drawing of optic probe assembly 300 in vessel 302. Bend portions 305A and 305B provide offset handle portion 307A and 307B to assist in inserting, withdrawing and adjusting the position of the probe within sample vessel 302. Bend portions 305A and 305B also minimize possible interferences with paddle drive components that are part of commercial test equipment.

In assembling of the preferred embodiments, a length of fiber (longer than the total length of the support tube member) is inserted into the curved tube portion and epoxied into place at the light path gap end. The fiber end may be either flush with the tube end or slightly extended with epoxy around the edges forming a sloping mound around the exposed fiber.

The preferred assembly method results in a polished fiber end that is flush with the tube end. The fiber end may be polished before or after inserting the fiber into the tubing. The preferred assembly procedure is to insert a length of fiber into the distal end of the tube. For large (greater than 5 mm.) sample gaps, the distal fiber end can be polished after being epoxied into place. For smaller sample gaps, the distal fiber end can be prepolished before inserting into the distal end of the tube. If the distal fiber end is polished after insertion, the fiber may be inserted at either the proximal or distal ends. The objective is to avoid damaging the distal fiber end.

The tubes of upper support assembly 301 are inserted over the fibers and attached to the elongated tube portions of probe 100 with epoxy. The upper fiber ends are prepared for termination in the SMA connector. These fiber-to-connector termination procedures, though non-trivial, are well known and routinely employed in the telecommunications industry. The SMA (or other) connector is inserted over the fiber and attached to the upper support assembly with epoxy. Epoxy is also applied inside the ferrule. The epoxy is allowed to dry and the final polish is applied to the SMA terminated fiber.

In other embodiments and assembly procedures, no connectors are used at the probe and the fibers are terminated at the spectrograph and the light source.

In the preferred embodiments, an adjustable probe holder or clamp 315, inserted in aperture or slot 317A of vessel cover 317 secures probe assembly 300 to vessel cover 317. Probe assembly 300 is secured by clamp screw 325 and nut 327 to grip connection tubes 303A and 303B, and provide a means to adjust the sample gap depth 319 in sample vessel 302. Vessel cover 317 comprises slot 317B for insertion of shaft 323 of paddle assembly 321. The operator will adjust he holder position depending on dissolution bath type, solution volume and vessel size.

Adhesives such as epoxy may be used to fix connection tubes 303A and 303B of upper support assembly 501 to optic probe section 100 at tube ends 331. Alternatively, welding or mechanical fasteners may fix upper support assembly 501 to optic probe section 100. Adhesives such as epoxies may also secure optic fibers 117A and 117B in tube members 107A and 107B at tube end 333. Adhesives such as epoxies may be used to secure optic fibers 311A and 311B in tubes 303A and 303B of upper support assembly 501. Optic connector 509 may be an optic connector known in the art such as an SMA type connector.

Figure 5:
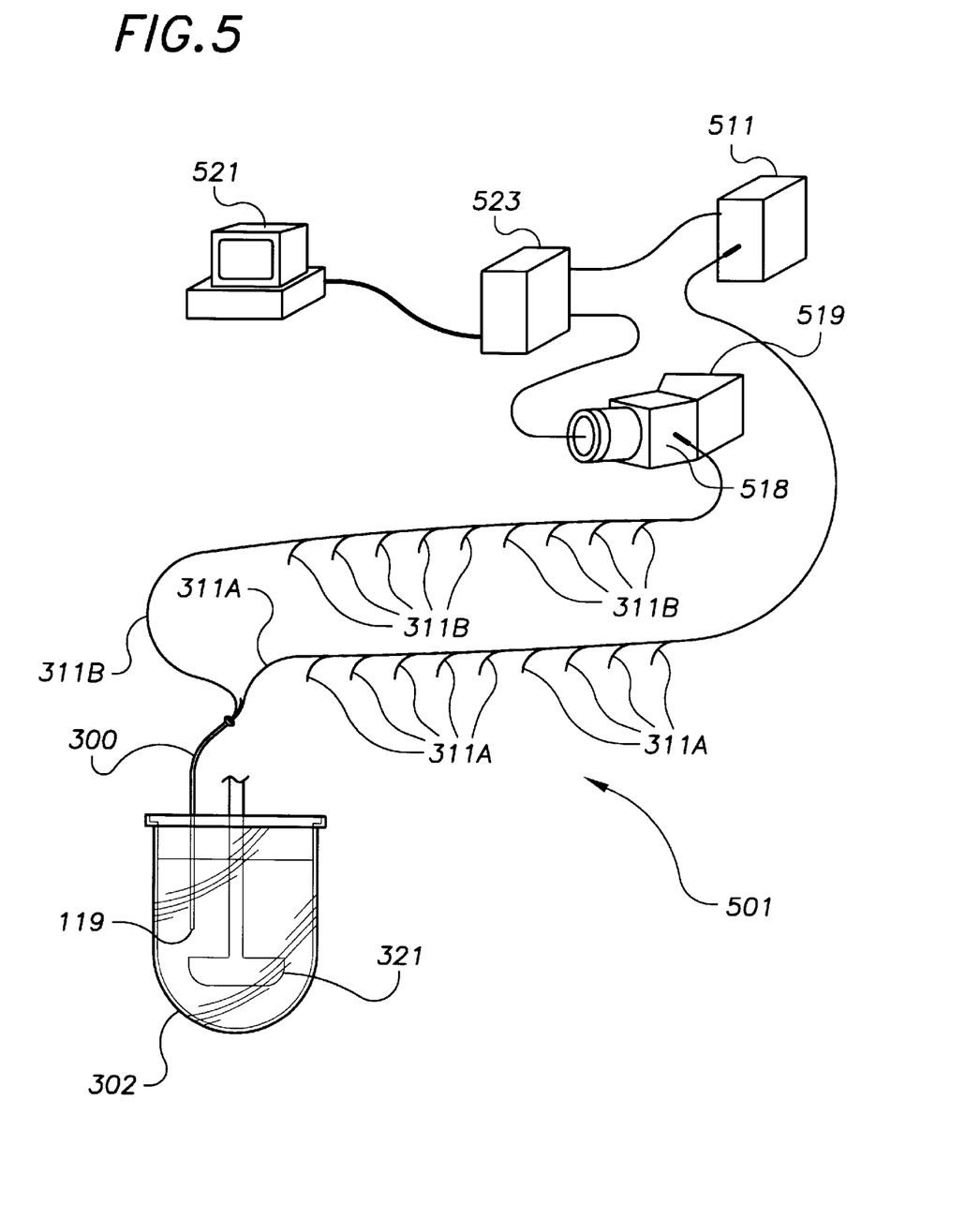
FIG. 5 is a schematic drawing of a multi-channel, fiber optic-based UV spectrometer system comprising ten optic probes of the present invention connected to a single spectrograph via multiple transmitting and receiving optic fibers.

FIG. 5 is a schematic diagram of a multi-channel, fiber optic-based UV spectrometer system 501 optimized for measuring the dissolution rates of pharmaceutical dosage forms. The basic measurement principle is identical to conventional UV spectroscopy, wherein dissolved component concentrations are proportional to the amount of light absorbed by the sample.

Multiple fiber optic probes, such as fiber optic probe 300 are illuminated with UV light through transmitting optic fibers 311A terminated at a low-noise deuterium light source 511.

Light passing through the sample gap 119 of probe 300 passes through receiving optic fibers 311B terminated at the inlet slit 518 to spectrograph 519. The spectrograph separates light into different wavelengths and simultaneously images the light beams onto a charge coupled device (CCD) detector.

Light intensity data is transferred to the computer 521, where software calculates and displays absorbance values and percent dissolved for each channel at user-selected time points and wavelengths. Controller 523 interfaces with computer 521 and provides control of light source 511 and spectrograph 519. Paddle assembly 321 provides desired agitation in vessel 302 as described previously. The lower end of the shaft is threaded to accept baskets and tablet dies used for intrinsic dissolution testing.

Ten or more vessels can be monitored simultaneously by coupling receiving fibers 311B to the CCD of spectrograph 519. Coupling ten or more probes such as probe 300 to a single CCD of a spectrograph is made possible by the efficient direct light path in sample gap 119 of probe 300. The direct light path allows small-diameter receiving fibers and hence a higher density of receiving fibers scanned by the CCD of spectrograph 519 than would be possible utilizing conventional probes utilizing additional optic elements such as mirrors, prisms, etc. The actual image acquisition time depends on the user-selected exposure or integration time (typically 100–1000 ms). In another preferred embodiment, at least 12 receiving fibers from sample vessels are monitored by a single spectrograph. In still another embodiment, at least 18 receiving fibers from sample vessels are monitored by a single spectrograph.

At each user-selected time point, the system software acquires and saves complete UV spectra for all configured channels. The collected data at a given time point is referred to as a "data set". The effect of different analytical wavelengths and/or baseline correction techniques can be immediately observed by changing the desired parameters.

Reference blank intensity spectra are acquired for both sample and standard blank solutions prior to the dissolution test. Prior to all image acquisitions the software automatically acquires a background or "dark current" reading that is subtracted from the light intensity reading. Since the background reading also contains a room light component, all light intensity and absorbance values are also corrected for any room light that may be entering through the fiber optic probes. The actual time required to acquire the background and sample intensities and transfer the data to the computer is typically 8–15 sec. This represents the minimum time between sample measurements.

Percent dissolved calculations are based on measurements of standard solutions and the expected amount of the target ingredient in the sample. The software has different options for correcting both sample and standard absorbance values for baseline variations related to turbidity, source drift, or light scattering.

FIGS. 6A–6D show alternative embodiments of optic probes which reduce hydraulic flow disturbances in a sample gap portion of the probe. In each of these embodiments, the longitudinal axis of the probe is defined by the elongated body portion of the probe. The longitudinal axis of the probe will normally be perpendicular to the surface of the fluid in a sample vessel.

Figure 6A:
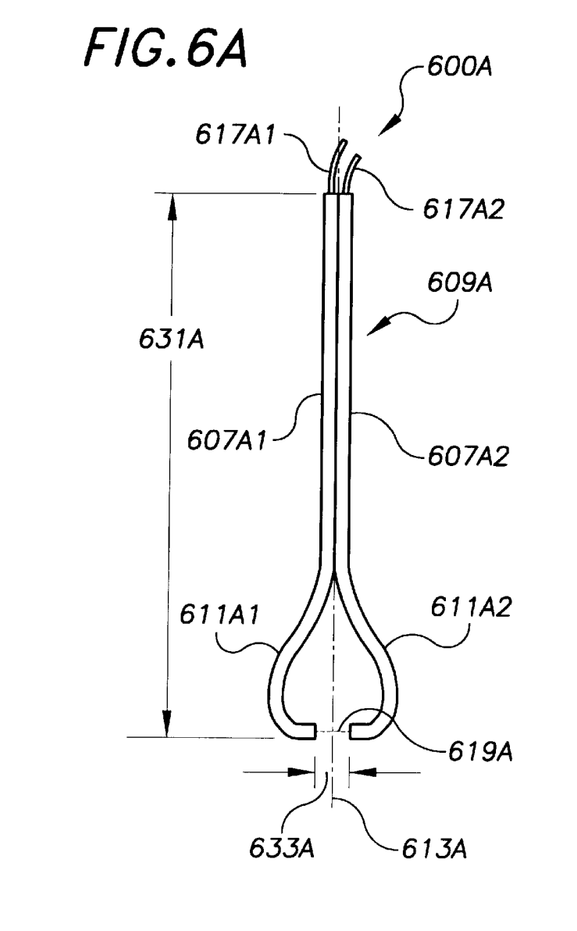
FIG. 6A is a front view of an alternative embodiment of the present invention showing an elongated tube portion and two lower curved tube portions having symmetric or mirror-image compound-curved tube portions providing a direct path light gap.

The elongated tube portion 609A of probe 600A comprises two elongated tubes 607A1 and 607A2, attached by welding, adhesives or mechanical fasteners. Tube portions 607A1 and 607A2 support optic fibers 617A1 and 617A2. Curved tube portions 611A1 and 611A2 comprise compound, "C" or "S" type bends to form sample gap 619A of length 633A perpendicular to longitudinal axis 613A. The curved tube portions may be symmetric as shown, or they may be non-symmetric. The diameter of lower curved tube portions 611A1 and 611A2 are small as compared to probe length 631A and follow the absolute dimensions as discussed in embodiment 100 of the optic probe to reduce hydraulic flow disturbances of the sample fluid, for example during tablet dissolution testing.

Figure 6B:
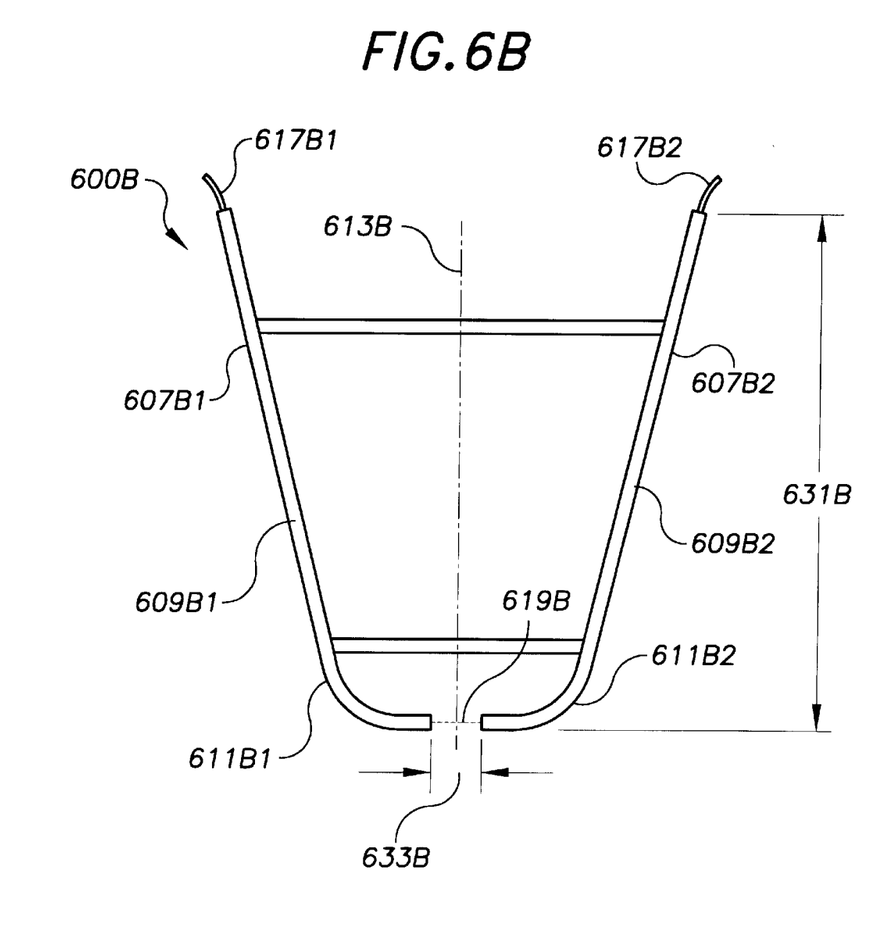
FIG. 6B is a front view of an alternative embodiment of that shown in FIG. 1 wherein the elongated body portion spreads or fans outward towards the proximal end.

FIG. 6B shows a variation 600B of embodiment 100 of the optic probe wherein elongated tube portions 609B1 and 609B2 of support tube members 607B1 and 607B2 are angled or "fanned" outward with respect to each other and longitudinal axis 613B from the distal to the proximal end of the probe. The angling out of the proximal ends of the elongated tube portions allows curved tube portions 611B1 and 611B2 to be less than 90 degrees, improving light transmission efficiency of the optic fibers. In other embodiments, only one elongated tube portion is angled out with respect to longitudinal axis 613B. In the preferred embodiments, sample gap 619B, of length 633B, is perpendicular to longitudinal axis 613B. The diameter of lower curved tube portions 611B1 and 611B2 are small as compared to probe length 631B and consistent with absolute dimensions as discussed in embodiment 100 of the optic probe to reduce hydraulic flow disturbances of the fluid, for example during tablet dissolution testing.

Figure 6C:
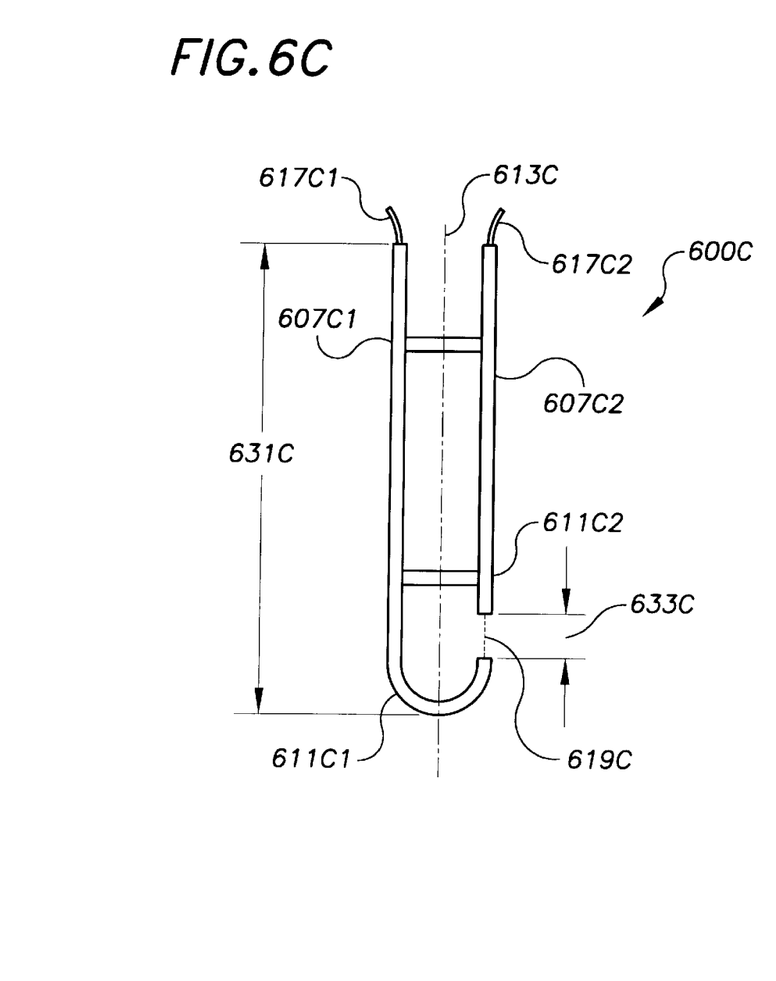
FIG. 6C is a front view of an alternative embodiment of the present invention showing a "U" shaped probe and a sample gap having a longitudinal axis parallel with the longitudinal axis of the probe.

FIG. 6C shows an alternative embodiment of "U"-shaped optic probe 600C having one support tube member 607C1 having a curved, substantially "J" shape and the second support tube member 607C2 substantially straight. This embodiment results in longitudinal axis of sample gap 619C, of length 633C, being approximately parallel to longitudinal axis 613C. The diameter of lower curved tube portion 611C1 and lower tube portion 611C2 are small as compared to probe length 631C and consistent with absolute dimensions as discussed in embodiment 100 of the optic probe to reduce hydraulic flow disturbances of the fluid, for example during tablet dissolution testing.

Figure 6D:
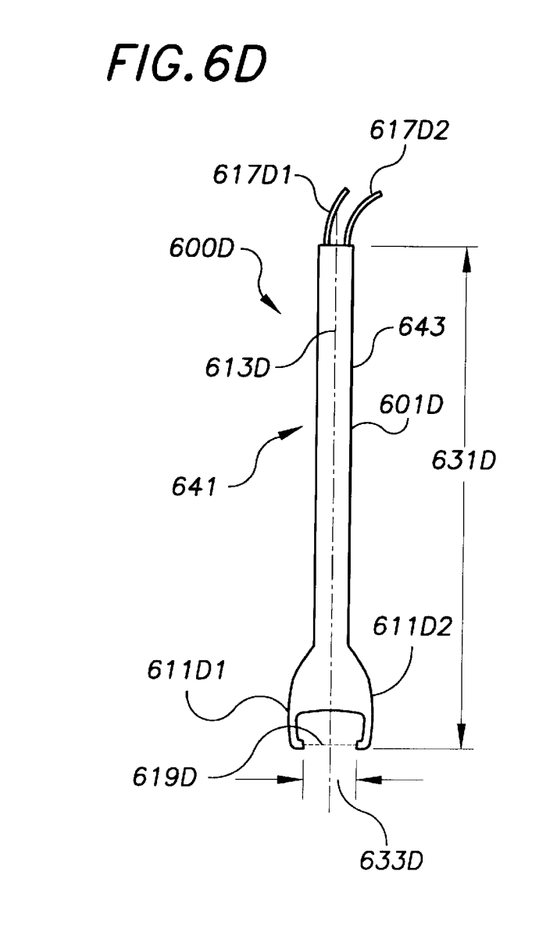
FIG. 6D is a front view of an alternative embodiment of the present invention having an integral body assembly.

FIG. 6D is an embodiment 600D of the optic probe similar to that of FIG. 6A except that elongated body portion 601D and extended leg portions 611D1 and 611D2 form an integral body assembly 641. Sample gap 619D, of length 633D, is perpendicular to longitudinal axis 613D. The diameter of extended leg portions 611D1 and 611D2 are small as compared to probe length 631D and consistent with absolute dimensions as discussed in embodiment 100 of the optic probe to reduce hydraulic flow disturbances of the fluid, for example during tablet dissolution testing.

In the preferred embodiments, a length of fiber (longer than total length of the support tube member) is inserted into the bent leg and epoxied into place at the light path gap end. The fiber end may be either flush with the tube end or slightly extended with epoxy around the edges forming a sloping mound around the exposed fiber. The fiber is then polished. This is repeated for both legs.

The tubes of upper support assembly 301 of FIG. 3 are inserted over the fibers and attached to the elongated tube portions of probe 100 with epoxy. The upper fiber ends are prepared for termination in the SMA connector. These fiber-to-connector termination procedures, though non-trivial, are well known and routinely employed in the telecommunications industry. The SMA (or other) connector is inserted over the fiber and attached to the upper support assembly with epoxy. Epoxy is also applied inside the ferrule. The epoxy is allowed to dry and the final polish is applied to the SMA terminated fiber. In other embodiments, the fibers are jacketed with flexible material routinely employed in the art and terminated using industry standard connectors directly to the light source and detector.

Other embodiments of the optic probe may utilize multiple transmitting or receiving optic fibers. Yet other embodiments may utilize relatively larger diameter receiving optic fibers, and its support tube in relation to the transmitting optic fibers and its support tube. For example, in the embodiment of FIG. 6C, fiber 617C2 may be selected as the receiving fiber and be a larger diameter fiber than transmitting fiber 617C1 in order to supply a larger amount of light energy at sample gap 619C. The higher light efficiency of sample gap 619C allows a smaller diameter fiber 617C1 and a relatively small bending radius of lower tube portion 611C1. Upper support assemblies, such as that shown in FIG. 5, may be utilized with these or equivalent probes, modified as required.

Accordingly, the reader will see that the fiber optic probe of the present invention provides an in vitro pharmaceutical dissolution testing optic fiber probe which improves performance and consistency of tablet dissolution testing. The device provides the following additional advantages:

The probe utilizes a direct light path without redirecting the light path with mirrors, prisms or other supplementary optic elements;

The probe reduced-diameter transmitting and receiving optic fibers allowed by the increase in optic efficiency of the direct light path gap, allows reduced-diameter probe components such as fiber support tubes and reduced hydraulic disturbances resulting from the smaller probe elements;

The reduced-diameter receiving fibers allow more channels of sample probes analyzed by a single CCD of a spectrograph; and The optic probes and dissolution test systems are simple and low in cost.

Although the description above contains many specifications, these should not be construed as limiting the scope of the invention but merely providing illustrations of some of the presently preferred embodiments of this invention. Thus the scope of the invention should be determined by the appended claims and their legal equivalents, rather than by the examples given.

I claim:

1. An optic fiber probe for sampling fluids in a sample vessel, the probe comprising:
   an elongated body portion insertable in the sample vessel, the elongated body portion defining a longitudinal axis of the probe;
   a first optic fiber supported internal to a first support member disposed on a distal end portion of the elongated body portion, a distal end of the first optic fiber defining a first optic surface at a distal end of the first support member;

a second optic fiber supported internal to a second support member disposed on the distal end portion of the elongated body portion, a distal end of the second optic fiber defining a second optic surface at a distal end of the second support member;

Each of said first optic fiber and said second optic fiber comprising a curved portion on said distal end portion of the elongated body portion wherein a first optic axis of the first optic fiber at the first optic surface and a second optic axis of the second optic fiber at the second optic surface are generally coincident and define a longitudinal axis of a sample gap at a distal end portion of the probe between the first optic surface and the second optic surface for direct electromagnetic wave communication between the first optic surface and the second optic surface;

the longitudinal axis of the sample gap being generally perpendicular to the longitudinal axis of the probe.

2. The probe of claim 1 wherein the first support member is a first tube supporting the distal end of the first optic fiber and the second support member is a second tube supporting the distal end of the second optic fiber.

3. The probe of claim 2 wherein the first tube and the second tube each comprise an elongated tube portion generally aligned with the longitudinal axis of the probe.

4. The probe of claim 2 wherein the first tube comprises an inner diameter selected to provide a loose tolerance fit with the first optic fiber.

5. The probe of claim 2 wherein the first tube comprises an inner diameter selected to provide a loose tolerance fit with the first optic fiber and the second tube comprises an inner diameter selected to provide a loose tolerance fit with the second optic fiber.

6. The probe of claim 5 comprising a first cross-member connecting the first tube with the second tube.

7. The probe of claim 6 wherein a cross-sectional area of the first cross-member is approximately the same as a cross-sectional area of the first tube.

8. The probe of claim 7 comprising a second cross-member connecting the first tube with the second tube.

9. The probe of claim 7 wherein the first tube and the second tube are made of stainless steel.

10. The probe of claim 1 wherein the elongated body portion comprises an elongated tube portion of the first support member and an elongated tube portion of the second support member.

11. The probe of claim 1 comprising a first cross-member connecting the first support member and the second support member.

12. The optic fiber probe of claim 1 wherein said curved portion on said first optic fiber and said second optic fiber comprises an angle of approximately ninety degrees.

13. The optic fiber probe of claim 1 wherein the first optic axis is perpendicular to the first optic surface and the second optic axis is perpendicular to the second optic surface.

14. An optic fiber probe for sampling fluids in a sample vessel, the probe comprising:

an elongated body portion defining a longitudinal axis of the probe; and a distal probe end portion comprising a first curved portion of a first support tube enclosing a first optic fiber, and a second curved portion of a second support tube enclosing a second optic fiber, and a cross-support connecting the first support tube and the second support tube so that a distal end of the first optic fiber and a distal end of the second optic fiber form a direct path sampling gap comprising a longitudinal axis generally perpendicular to the longitudinal axis of the probe.

15. The probe of claim 14 wherein the cross-support is a cross-member connected to the curved portion of the first support tube.

16. The probe of claim 14 wherein the cross-support is a cross-member connected to the first curved portion of the first support tube and the second curved portion of the second support tube.

17. The probe of claim 14 wherein the cross-support comprises a cross-member connected to an elongated portion of the first support tube and an elongated portion of the second support tube.

18. The probe of claim 17 wherein the cross-support comprises a first cross-member connected to the elongated portion of the first support tube and the elongated portion of the second support tube and a second cross-member connected to the first curved portion of the first support tube and the second curved portion of the second support tube.

19. The probe of claim 14 wherein the cross-support comprises a weld portion connecting the first support tube and the second support tube.

20. The probe of claim 14 wherein the cross-support comprises an adhesive connecting the first support tube and the second support tube.

21. The probe of claim 14 wherein the elongated body portion is a body tube enclosing the first optic fiber and the second optic fiber and a distal end of the body tube is connected to a proximate end of the first curved portion of the first support tube and the second curved portion of the second support tube.

22. A low flow-disturbance probe for dissolution testing, the probe comprising:

an elongated body portion defining a longitudinal axis of the probe and a distal end portion, the distal end portion comprising a first small-diameter support tube portion supporting a first optic fiber; and a second small-diameter support tube portion supporting a second optic fiber;

the first small-diameter support tube portion and the second small-diameter support tube 10 portion defining a sample gap having a direct light path between a first optic surface of the first optic fiber and a second optic surface of the second optic fiber;

said first small-diameter support tube portion comprising a curved portion at said distal end to align an optic axis of said first optic fiber with an optical axis of said second optic fiber.

23. The low flow-disturbance probe of claim 22 wherein the probe comprises a probe length along an axis parallel to the longitudinal axis and a predetermined diameter of said first small-diameter support tube portion is less than 0.05 of the probe length.

24. The low flow-disturbance probe of claim 22 wherein the probe comprises a probe length along an axis parallel to the longitudinal axis and a predetermined diameter of said first small-diameter support tube portion is less than 0.02 of the probe length.

25. The low flow-disturbance probe of claim 22 wherein a predetermined diameter of said first small-diameter support tube portion is less than 1.5 mm.

26. The low flow-disturbance probe of claim 22 wherein a predetermined diameter of said first small-diameter support tube portion is less than 1.0 mm.

27. The low flow-disturbance probe of claim 22 wherein a predetermined submerged displacement volume of the probe is less than 200 cubic millimeters.

28. The low flow-disturbance probe of claim 22 wherein a predetermined submerged displacement volume of the probe is less than 100 cubic millimeters.

29. The low flow-disturbance probe of claim 22 wherein a predetermined submerged displacement volume of the probe is less than 50 cubic millimeters.

30. A multi-channel, fiber optic-based spectrometer system for measuring the dissolution rates of pharmaceutical dosage forms comprising:

a plurality of fiber optic probes, each of said plurality of fiber optic probes comprising an elongated body portion defining a longitudinal axis, a transmitting optic fiber and a receiving optic fiber, a transmitting optic fiber end surface and a receiving optic fiber end surface axially aligned by a curved support tube enclosing said transmitting optic fiber on a distal end portion of said each of said plurality of fiber optic probes and spaced to define a sample gap generally perpendicular to the longitudinal axis of the optic probe and comprising a direct light path between the transmitting optic fiber end surface and the receiving optic fiber end surface; and a means for connecting said plurality of fiber optic probes to a single light source and a single spectrograph comprising a charged coupled device.

* * * * *